United States Patent
Oung et al.

(10) Patent No.: US 7,079,888 B2
(45) Date of Patent: Jul. 18, 2006

(54) METHOD AND APPARATUS FOR MONITORING THE AUTONOMIC NERVOUS SYSTEM USING NON-STATIONARY SPECTRAL ANALYSIS OF HEART RATE AND RESPIRATORY ACTIVITY

(75) Inventors: Harry Oung, Philadelphia, PA (US); Joseph Colombo, Richboro, PA (US)

(73) Assignee: Ansar, Inc., Philadelphia, PA (US)

( * ) Notice: Subject to any disclaimer, the term of this patent is extended or adjusted under 35 U.S.C. 154(b) by 471 days.

(21) Appl. No.: 10/387,070

(22) Filed: Mar. 12, 2003

(65) Prior Publication Data

US 2004/0111033 A1    Jun. 10, 2004

Related U.S. Application Data

(60) Provisional application No. 60/371,909, filed on Apr. 11, 2002.

(51) Int. Cl.
*A61B 5/0402* (2006.01)
(52) U.S. Cl. .................................................. 600/513
(58) Field of Classification Search ......... 600/508–523
See application file for complete search history.

(56) References Cited

U.S. PATENT DOCUMENTS

| | | | |
|---|---|---|---|
| 3,989,034 A | 11/1976 | Hojaiban | |
| 4,018,219 A | 4/1977 | Hojaiban | |
| 4,510,944 A | 4/1985 | Porges | |
| 4,832,038 A | 5/1989 | Arai et al. | |
| 4,862,361 A | 8/1989 | Gordon et al. | |
| 4,930,517 A | 6/1990 | Cohen et al. | |
| 4,979,110 A | 12/1990 | Albrecht et al. | |
| 5,042,497 A | 8/1991 | Shapland | |
| 5,042,499 A | 8/1991 | Frank et al. | |
| 5,105,354 A | 4/1992 | Nishimura | |
| 5,191,524 A | 3/1993 | Pincus et al. | |
| 5,265,617 A | 11/1993 | Verrier et al. | |
| 5,285,793 A | 2/1994 | Slovut et al. | |
| 5,411,031 A | 5/1995 | Yomtov | |
| 5,423,325 A | 6/1995 | Burton | |
| 5,437,285 A | 8/1995 | Verrier et al. | |
| 5,466,245 A | 11/1995 | Spinelli et al. | |
| 5,481,269 A | 1/1996 | Imhoff et al. | |
| 5,495,554 A | 2/1996 | Edwards et al. | |
| 5,503,159 A | 4/1996 | Burton | |
| 5,522,854 A | 6/1996 | Ideker et al. | |
| 5,537,344 A | 7/1996 | Isshiki et al. | |
| 5,562,596 A | 10/1996 | Pincus et al. | |
| 5,596,993 A | 1/1997 | Oriol et al. | |

(Continued)

FOREIGN PATENT DOCUMENTS

EP    0944411 B1    4/2001

(Continued)

*Primary Examiner*—Scott M. Getzow
(74) *Attorney, Agent, or Firm*—Mark D. Simpson; Synnestvedt & Lechner LLP

(57) ABSTRACT

A method and apparatus for non-invasive, real-time monitoring of the autonomic nervous systems using non-stationary spectral analysis of both heart rate and respiratory signals. Continuous wavelet transformation is used in real-time so that the dynamic interactions between the sympathetic and parasympathetic divisions of the autonomic nervous system can be independently monitored in the frequency domain. The method in accordance with the present invention allows spectral analysis, formerly limited to the study of stationary data, to be applied to time-varying biological data such as heart rate variability and respiratory activity. In addition, the same techniques are used to monitor other biological or physiological data, including blood pressure.

28 Claims, 3 Drawing Sheets

U.S. PATENT DOCUMENTS

| | | |
|---|---|---|
| 5,603,331 A | 2/1997 | Heemels et al. |
| 5,622,178 A | 4/1997 | Gilham |
| 5,682,901 A | 11/1997 | Kamen |
| 5,712,801 A | 1/1998 | Turcott |
| 5,718,235 A | 2/1998 | Golosarsky et al. |
| 5,749,900 A | 5/1998 | Schroeppel et al. |
| 5,767,160 A | 6/1998 | Kaesemeyer |
| 5,769,793 A | 6/1998 | Pincus et al. |
| 5,810,737 A | 9/1998 | Dardik |
| 5,842,997 A | 12/1998 | Verrier et al. |
| 5,846,189 A | 12/1998 | Pincus |
| 5,891,044 A | 4/1999 | Golosarsky et al. |
| 5,919,210 A | 7/1999 | Lurie et al. |
| 5,921,940 A | 7/1999 | Verrier et al. |
| 5,952,957 A | 9/1999 | Szu |
| 5,957,855 A | 9/1999 | Oriol et al. |
| 5,964,788 A | 10/1999 | Greenhut |
| 5,967,995 A | 10/1999 | Shusterman et al. |
| 6,009,447 A | 12/1999 | Kubota et al. |
| 6,026,230 A | 2/2000 | Lin et al. |
| 6,035,233 A | 3/2000 | Schroeppel et al. |
| 6,050,950 A | 4/2000 | Mohler |
| 6,050,951 A | 4/2000 | Friedman et al. |
| 6,053,872 A | 4/2000 | Mohler |
| 6,078,834 A | 6/2000 | Lurie et al. |
| 6,144,877 A | 11/2000 | DePetrillo |
| 6,144,878 A | 11/2000 | Schroeppel et al. |
| 6,152,879 A | 11/2000 | Mohler |
| 6,169,919 B1 | 1/2001 | Nearing et al. |
| 6,179,783 B1 | 1/2001 | Mohler |
| 6,212,427 B1 | 4/2001 | Hoover |
| 6,216,032 B1 | 4/2001 | Griffin et al. |
| 6,229,453 B1 | 5/2001 | Gardner et al. |
| 6,253,107 B1 | 6/2001 | Albrecht et al. |
| 6,253,175 B1 | 6/2001 | Basu et al. |
| 6,269,263 B1 | 7/2001 | Ohnishi et al. |
| 6,277,875 B1 | 8/2001 | Holman |
| 6,301,499 B1 | 10/2001 | Carlson et al. |
| 6,308,094 B1 | 10/2001 | Shusterman et al. |
| 6,310,963 B1 | 10/2001 | Erdol et al. |
| 6,330,469 B1 | 12/2001 | Griffin et al. |

FOREIGN PATENT DOCUMENTS

| | | |
|---|---|---|
| JP | 08095955 A | 12/1996 |

METHOD AND APPARATUS FOR MONITORING THE AUTONOMIC NERVOUS SYSTEM USING NON-STATIONARY SPECTRAL ANALYSIS OF HEART RATE AND RESPIRATORY ACTIVITY

REFERENCE TO RELATED APPLICATION

This application claims priority to U.S. Provisional Application No. 60/371,909, filed Apr. 11, 2002, which is hereby incorporated by reference.

FIELD OF THE INVENTION

The present invention relates, in general, to systems for monitoring the autonomic nervous system, and more specifically to a system for using real-time heart rate spectral analysis and wavelet transformation for monitoring the autonomic nervous system.

BACKGROUND OF THE INVENTION

The autonomic nervous system regulates involuntary functions of nearly all parts of the body in health and disease. It is comprised of two main subdivisions known as the sympathetic nervous system (sympathetic system) and the parasympathetic nervous system (parasympathetic system). The sympathetic system is the system that helps the body respond to stressful situations, and is often referred to as the "fight or flight" system. For example, under stressful conditions the sympathetic system increases the rate in which neurons are fired in order to increase the heart rate, elevate blood pressure, and slow down the digestive process. In contrast, the parasympathetic system helps the body preserve and restore energy. It is often referred to as the "rest and digest" system. For example, when one relaxes by resting in a chair, the parasympathetic system slows the heart, lowers blood pressure, and speeds the digestive process.

Under normal resting or sleeping conditions, the parasympathetic system is dominant. The sympathetic system is normally activated with the addition of external stressful conditions. However, certain conditions such as chronic stress, disease, and emotion, can alter the natural balance between the parasympathetic system and the sympathetic system. These factors generally create a persistent elevation in activity in the sympathetic system and a reduction in activity in the parasympathetic system or vise versa. If not controlled, such an imbalance in the autonomous nervous system can impair the functioning of many organs including the heart, vasculature, gastrointestinal (GI) track, kidneys, and lungs. Such impairment can lead to conditions such as altered blood pressure, heart disease, vascular disease, GI track immobility, kidney failure, and other organ related conditions.

Today, medications are available that affect the autonomic nervous system, such as ACE-inhibitors, beta-blockers, and anti-depressants. These medicines are used to treat altered blood pressure, irregular heart rhythm, chronic fatigue, diabetes, depression, and other conditions related to the autonomic nervous system. These medicines affect the synthesis, release, uptake, and re-uptake of the body's neural chemistry by acting on the receptors in neurons or muscles located in the various areas of the body, such as the brain, heart, kidney, and blood vessels. Many patients use several of these medications simultaneously; thus, it is increasingly important to be able to measure the response of the autonomic nervous system to ensure that the medications are having the desired effects and that a combination of medications is not creating an undesirable imbalance in the autonomic system.

Injury and disease can also have an affect on the autonomic nervous system. For example, diabetes often leads to a condition known as Diabetic Autonomic Neuropathy, which is a condition whereby there is damage to the autonomic nerves. This, in turn, can lead to poor peripheral blood flow, GI track immobility, sexual dysfunction, kidney disease, blindness and silent myocardial ischemia. Silent myocardial ischemia is a condition whereby the patient experiences episodes of blood flow constriction to the heart muscle that is often unnoticed because of an absence of chest pain due to a concurrent loss of sensory neurons. Conditions such as these require that the autonomic nervous system be closely and accurately monitored.

An effective method to monitor the autonomic nervous system is to monitor the function of the heart and the lungs and use the information gathered to derive information regarding the autonomic nervous system. In other words, the heart can be used as a "window" through which it is possible to study the activity of the autonomic nervous system. Heart rate is equal to the number of heartbeats occurring within a specific length of time, and is normally measured in beats per minute (bpm). For example, heart rates above 100 bpm (known as tachycardia) are generally considered to result from activity in the sympathetic system, while heart rates below 60 bpm (known as bradycardia), are generally considered to result from the activity in the parasympathetic system.

However, because the heart rate is influenced over time by both the sympathetic and parasympathetic systems, the average or mean heart rate is not the optimum indicator for monitoring the state of balance within the autonomic nervous system. A better picture can be derived using the instantaneous heart rate. The instantaneous heart rate can be determined by measuring the time interval between two heartbeats using a standard electrocardiogram (EKG). An accelerating heart rate will exhibit a decreasing time interval between beats, while a decelerating heart rate will exhibit an increasing time interval between beats. By measuring spontaneous changes in heart rate, the autonomic nervous system can be monitored more accurately. The parasympathetic system can cause a very fast response, capable of being observed on the next heartbeat (1 to 3 seconds), while response to sympathetic system activity is typically slower, often taking more than five heart beats (10 to 20 seconds). This makes it possible to distinguish activity within the two systems by observing the characteristics of the heart rhythm using frequency-domain analysis, which is well known in the art.

Frequency-domain analysis is a type of spectral analysis typically performed using mathematical modeling methods such as Fast Fourier Transforms (FFT) or autoregressive (AR) techniques. These techniques are used to study the frequency content of the instantaneous heart rate. In applying these techniques, a data sample is obtained over a five minute period (for short term studies) or a 24 hour period (for long-term studies). FFT and AR techniques can be used to process the data sample to separate the slow responding sympathetic activities from the quicker responding parasympathetic activities. However, because these frequency domain techniques do not provide for a means to locate the time events occurring within a data sample, they are most useful for studying short term steady state conditions, meaning situations where the data is consistent across the sample time. For short term studies, this requires the patient to remain motionless during the time period (typically five minutes) in which the data is being gathered. Patient movement, including small movements such as coughing and talking, can cause the accuracy of the information gathered to decrease.

In order to compensate for this shortcoming in pure frequency domain analysis, techniques have been used to modify the FFT and AR techniques to approximate a time domain analysis in addition to a frequency domain analysis. A short term FFT can be performed on smaller blocks of data from within the data sample, as opposed to using the entire data sample. This technique assumes that the data is quasi-stationary, and uses a sliding window within the data sample for choosing the data to analyze. This introduces a time dependent factor or time dependent localization into the analysis. However, this technique results in a trade-off between frequency domain analysis and time domain analysis. Choosing shorter windows within the data results in poorer frequency resolution, while increasing the window length decreases the time domain resolution. This shortcoming can create inaccuracies in the analysis of many types of biological data.

To address these inaccuracies, newly developed advanced mathematical techniques have been employed, such as the Wigner distribution and the Cohen class of time frequency distributions. However, these processes are quadratic in nature; thus, they produce undesirable cross-terms and interferences. This makes their usefulness in analyzing biological data limited. More recently, the technique of wavelet transformation has been considered as a means for processing heart rate data. Wavelet transformation is a mathematical technique known in the art. The technique is effective for analyzing transient variations within a time series, and thus appears to be well suited for spectral analysis of non-stationary signals such as those found in biological data. However, the complexity of wavelet transformation techniques has made real-time implementation difficult prior to the present invention.

What is needed is an effective, non-invasive method of analyzing biological data including the instantaneous heart rate and the respiratory activity to provided accurate, meaningful autonomic nervous system assessment from real-time heart rate variability data. Additionally, it is desirable to shorten the analysis period and improve the resolution of the processed results. This information can then be used to monitor the autonomic nervous system more accurately than previously possible, and further assist medical personnel in the diagnosis and treatment of related conditions.

SUMMARY OF THE INVENTION

The present invention is a method and apparatus for non-invasive, real-time monitoring of the autonomic nervous systems. The present invention allows for monitoring of the autonomic nervous system using non-stationary spectral analysis of both heart rate and respiratory signals.

A preferred embodiment uses continuous wavelet transformation in real-time so that the dynamic interactions between the sympathetic and parasympathetic divisions of the autonomic nervous system can be independently monitored in the frequency domain. The method in accordance with the present invention allows spectral analysis, formerly limited to the study of stationary data, to be applied to time-varying biological data such as heart rate variability and respiratory activity. In addition, a preferred embodiment of the present invention uses the same techniques to monitor other biological or physiological data, including blood pressure.

The present invention applies the technique of continuous wavelet transforms to input signals obtained from various physiological sensors. The technique provides a frequency domain analysis of the instantaneous heart rate that can be quickly and accurately obtained and is less sensitive to errors resulting from patient movement during the monitoring time period.

DETAILED DESCRIPTION OF THE INVENTION

A preferred embodiment of the present invention provides a method and apparatus for autonomic nervous system monitoring. Inputs from three sources are obtained and processed using continuous wavelet transforms and standard time-domain analysis. The results of the processing are displayed at an output (e.g., a video monitor).

Figure 1:
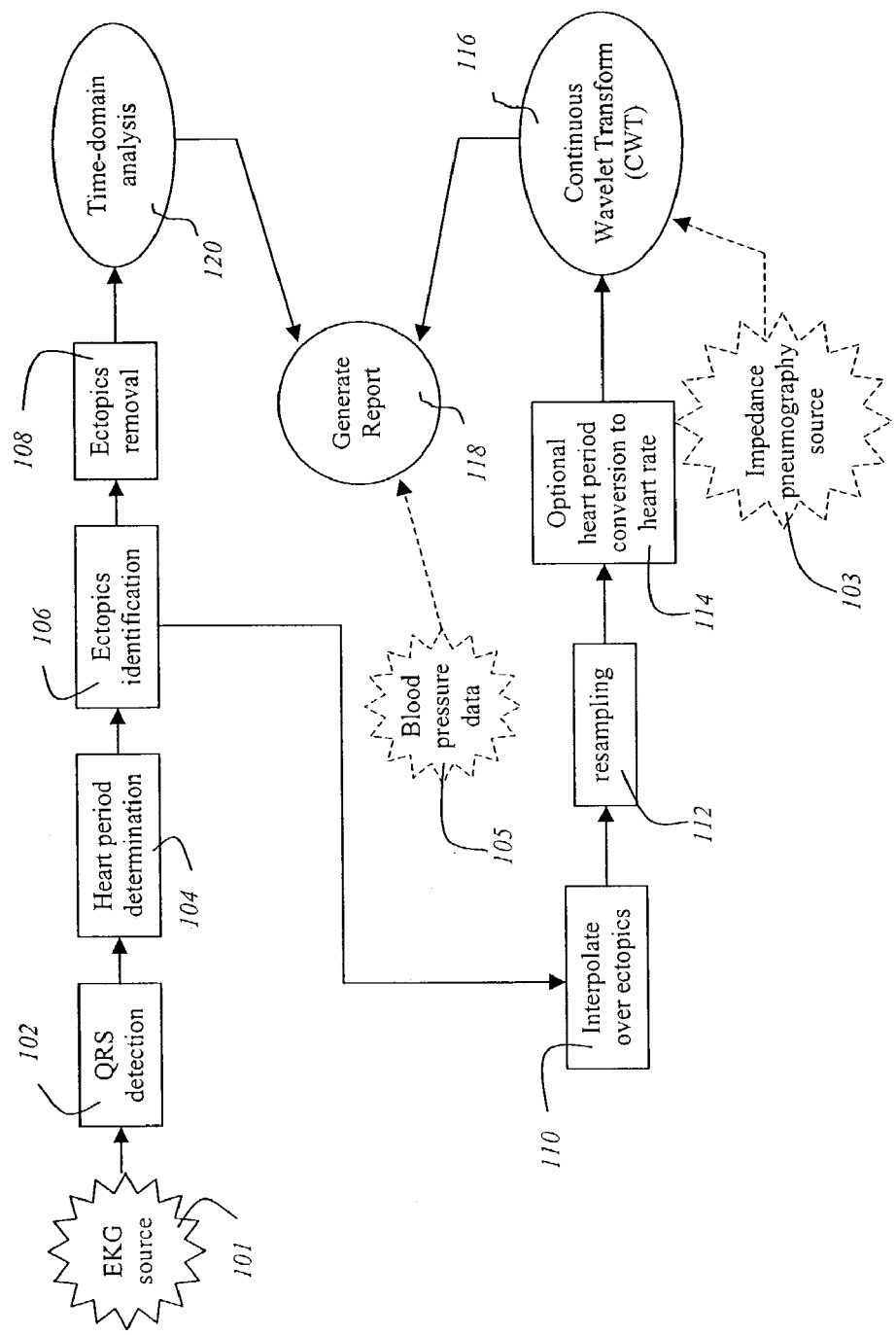
FIG. 1 is diagram of the patient monitoring process in accordance with the present invention.

FIG. 1 is a graphical illustration of the system in accordance with a preferred embodiment of the present invention. In a preferred embodiment, input is gathered from three sources. The three input sources are the EKG source 101, the impedance pneumography source 103, and the blood pressure source 105. Methods to gather the data at each source are well known in the art, and thus are not discussed herein in detail. The EKG source, which measures electrical impulses from the heart, is sampled at a minimum sampling rate of 250 samples per second, and a more preferred rate of 1000 samples per second, so that the heart beat intervals can be measured precisely within a few milliseconds.

The impedance pneumogram source 103 measures relative changes in thoracic impedance. During inspiration, the lung tissue fills with air and becomes more resistive to electricity, and the chest wall becomes thinner as its circumference increases. Both effects increase the impedance associated with the lung. This change in impedance can be measured by applying a small current (less than 300 microamps) between two surface electrodes, and monitoring the slight changes in voltage that occur during the breathing process.

The blood pressure source 105 monitors the patient's blood pressure using a non-invasive blood pressure measuring method such as the oscillometric method for burst assessment or the Finapres method for continuous assessment. A preferred embodiment uses the Finapres method, which provides the data required to perform a blood pressure variability analysis using wavelet transforms in accordance with the present invention. In a preferred embodiment, each input signal is displayed in real-time on an output display 107, while at the same time being concurrently processed in accordance with the present invention.

Figure 2:
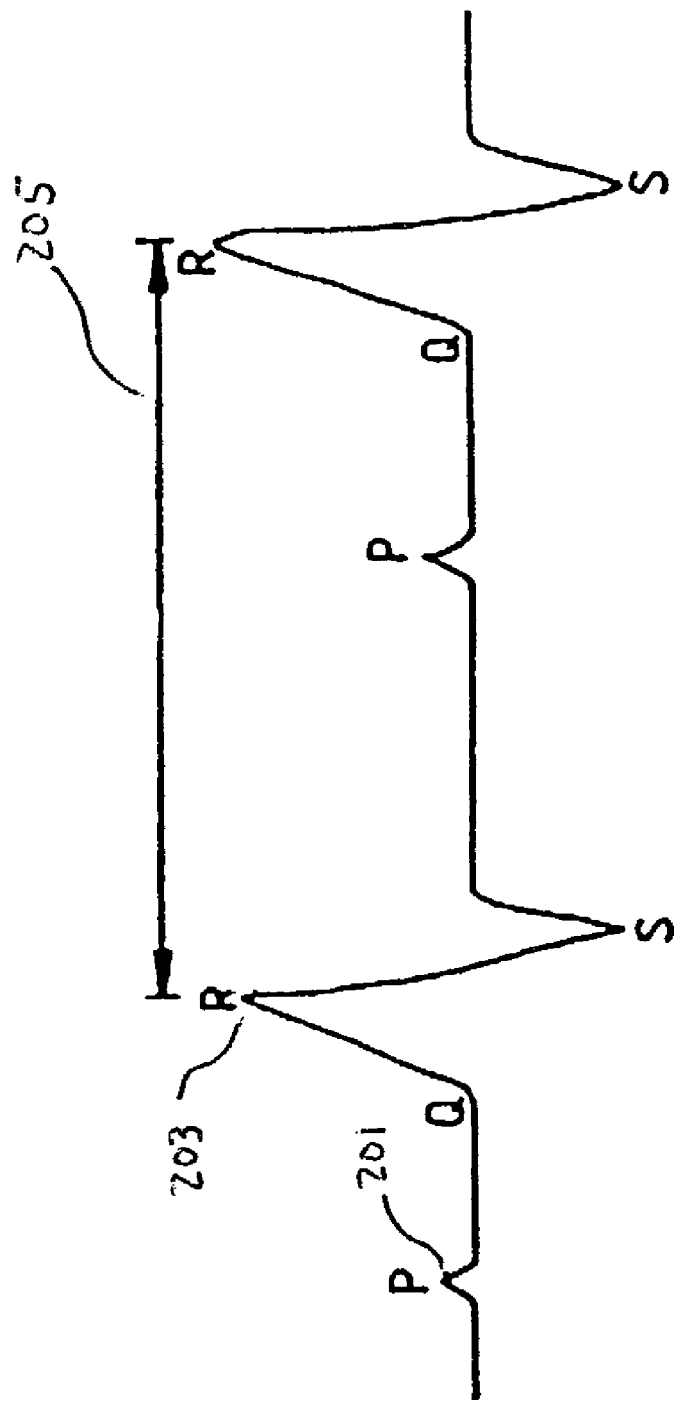
FIG. 2 is an illustration of an EKG signal.

The first step in conducting a heart rate analysis in accordance with the present invention is to identify the fiducial point (P point) of the EKG signal, as well as the other defined points (i.e., R point, Q point, and S point) on the EKG signal (step 102). The fiducial point is the beginning point of movement of the heart that constitutes a heartbeat. An EKG signal can be represented by a waveform as shown in FIG. 2. The fiducial point on the wave corresponds to the start of atrial depolarization and is referred to as the P point 201. Atrial depolarization begins in the sinoatrial (SA) node which is controlled by the autonomic nervous system. The R peak 203 of the wave is detected according to FDA approved methods well known in the art. The R-point corresponds to the point of maximum ventricular depolarization. This nomenclature is well known in the art.

Next, the period of the heartbeat is determined (step 104). The time between the onset of one heartbeat (P point) and the onset of the next heartbeat represents the period of the heart. However, because the R peak point is more easily identified than the P point, and the P-R interval is relatively constant in the absence of a conductive disorder of the heart, the generally accepted practice is to use the time interval between two consecutive R peaks 205 as the measure of the heart period. To identify the R peaks, the EKG signal is first filtered using a band-pass filter to reduce noise that could distort the wave. The R peaks are then identified using a differentiation and threshold algorithm to produce a pulse train, from which it is possible to identify when the derivative exceeds a set threshold. Once the R peaks are identified, the time interval between the peaks can be computed by using the pulse train to start and reset a clock. The result is a sequence of R-R durations known in the art as the RR-interval tachogram.

The next step in processing the EKG signal in accordance with the present invention is to identify any ectopics or missing beats (step 106). The ectopics are removed for the purposes of time domain analysis (step 108); however, a correction process is needed in order to perform accurate frequency domain analysis. Electrical activity in the heart can affect heart rate variability analysis by causing abnormal heart beat interval wave formation. It is important not to confuse these disturbances with the modulation signal from the brain to the SA node. Thus, these erroneous signals need to be removed before performing the spectral analysis on the RR-interval tachogram or instantaneous heart rate waveform. Using interpolation, these disturbances or ectopics are removed to provide the corrected heart rate signal, as described below.

Premature beats are characterized by a short beat-to-beat interval, followed by a longer than normal beat-to-beat interval. This will produce a sharp transient in the instantaneous heart rate wave. These beats can be identified using a mathematical algorithm. For example, the function r(n) defines the R-R interval of heart beat number n. The time of the $n^{th}$ heart beat is defined by the following:

T(n)=Sum{r(i)} where the summation is performed from i=0 to i=n. If the ratio r(n)/r(n−1) is larger than (1+x) where x is a predetermined threshold, then r(n) and r(n−1) are considered incorrect and tagged for correction.

Additionally, a R-R interval histogram can be used to identify incorrect beats. The R-R intervals associated with an incorrect beat are generally significantly shorter or significantly longer than the normal R-R intervals, and correspondingly fall outside the major concentration of the histogram. A histogram can be computed for every 30 successive R-R intervals. The $25^{th}$ and $75^{th}$ percentiles of the histogram are identified. A small central region (e.g., the $10^{th}$ beat to the $20^{th}$ beat) within the 30 R-R intervals is then examined. If an R-R interval is larger than the $75^{th}$ percentile (plus a predetermined threshold) or smaller that the $25^{th}$ percentile (less a predetermined threshold), the interval is deemed incorrect.

In accordance with the present invention, these two techniques are combined to accurately identify incorrect, missing, or premature beats. Once identified, these errors can be automatically corrected by applying a spline interpolation process (step 110) using the correct R-R intervals and their corresponding t(n) as inputs. The signal is re-sampled using the interpolation results (step 112). This assures that these disturbances do not corrupt the analysis, and that any subsequent spectral analysis is performed on an evenly sampled, discrete time signal as opposed to the original unevenly sampled R-R interval tachogram. In some embodiments, it is desired to convert the measurement of R-R intervals (heart period) into an instantaneous heart rate, expressed in bpm (step 114). This is accomplished by using the following relationship: Heart rate=60/heart period.

Once any errors resulting from ectopics or missing beats have been identified and corrected, the signal is processed using continuous wavelet transform techniques (step 116). Continuous wavelet transform of a discrete time series x(n) is computed as the convolution of x(n) with a scaled and translated version of a basis function h(t) such that:

$$CWT(n, f) = \Delta t \kappa(s) \sum_{\mu} x(\mu) h * \left(\frac{n-\mu}{s}\Delta t\right), \text{ for } s = f_0/f$$

whereby:

$\Delta t$ is the sampling period;

$\kappa(s)$ is a normalizing parameter that depends on the scale factor 's';

* represents complex conjugate;

$f_0$ is a constant reference.

For a small, nonzero value of s, the wavelet is a time-compressed function of the original basis function h(t), which corresponds to higher frequencies. For a large value of s, the wavelet is a time-dilated function of the original basis function h(t), which corresponds to lower frequencies. Thus, high frequency signal components are analyzed with a sharper time-resolution than low frequency components. By adjusting the scale factor 's' and translating the function h(t) along the time axis, a two-dimensional image is constructed from a one-dimensional time series. This enables the underlying signal features to be displayed both versus frequency and versus time. Conceptually, the continuous wavelet transform can be considered as a mathematical microscope in which one can observe different parts of the signal by just adjusting the focus (scale). In accordance with a preferred embodiment of the present invention, the wavelet power spectrum of concern is represented by the following:

$$P_{CWT}(n, f) = |CWT(n, f)|^2, \text{ for } x(n) \text{ complex}$$
$$= 2|CWT(n, f)|^2, \text{ for } x(n) \text{ real}$$

In order to ensure that this is a valid power distribution representation of the measured signal, a normalizing factor is applied. Normalization is crucial to assure that the power spectrum is affected only by the amplitude of the signal, and not by the wavelet function itself or the sampling frequency used. A normalizing factor $\kappa(s)$ is chosen such that:

$$\kappa^2(s)\Delta t \sum_{\mu} \left| h\left(\frac{\mu}{s}\Delta t\right) \right|^2 = 1$$

In accordance with a preferred embodiment of the present invention, the basis function h(t) is chosen to consist of a complex oscillating wave modulated by a Gaussian envelope:

$$h(t) = \exp\left(-\frac{18t^2 f_0^2}{Q^2} + j2\pi f_0 t\right)$$

whereby:

Q is a constant quality-factor that controls the resolution or quality of the wavelet analysis; and $f_0$ is the frequency of the oscillation (at scale s=1).

This allows for a direct correspondence between scale and frequency. The first term within the exponential function controls the shape of the envelope function, while the second term is a complex argument that contributes to the oscillations. For a small value of Q, the Gaussian envelope is narrow so the basis function contains just a few oscillating cycles. For a large value of Q, the envelope is wide so there are more cycles of oscillation contained in the basis function. For heart rate spectral analysis in accordance with the preferred embodiment, the value chosen in this invention is Q=5, so that the wavelet function at each scale would enclose five cycles of oscillation.

Once the basis function is chosen, it is necessary to choose a set of scales s for use in the wavelet spectral computation. Because frequency resolution varies as a function of the scale factor, it is convenient to compute the wavelet convolution as fractional powers of two, rather than over uniform increments:

$$s(i) = (2^\delta)^i, \quad i = 0, 1, \ldots, I$$

$$I = \frac{1}{\delta} \log_2\left(\frac{f_0}{\Delta f}\right)$$

whereby δ determines how frequent the sampling in scale is performed in the wavelet transform computation;

I determines the largest scale used in the computation;

Δf is the lowest frequency of interest in the analysis; and $f_0$ the highest frequency of interest.

For heart rate analysis in accordance with a preferred embodiment of the present invention, the set of values chosen is δ=⅕ to give adequate sampling in scale. Δf is equal to ⅟300Hz and $f_0$ is equal to 256Δf. The resulting wavelet spectrum $P_{CWT}(n,f)$ can then be linearly interpolated to fit on a rectangular grid of time and frequency and presented as an image.

Figure 3:
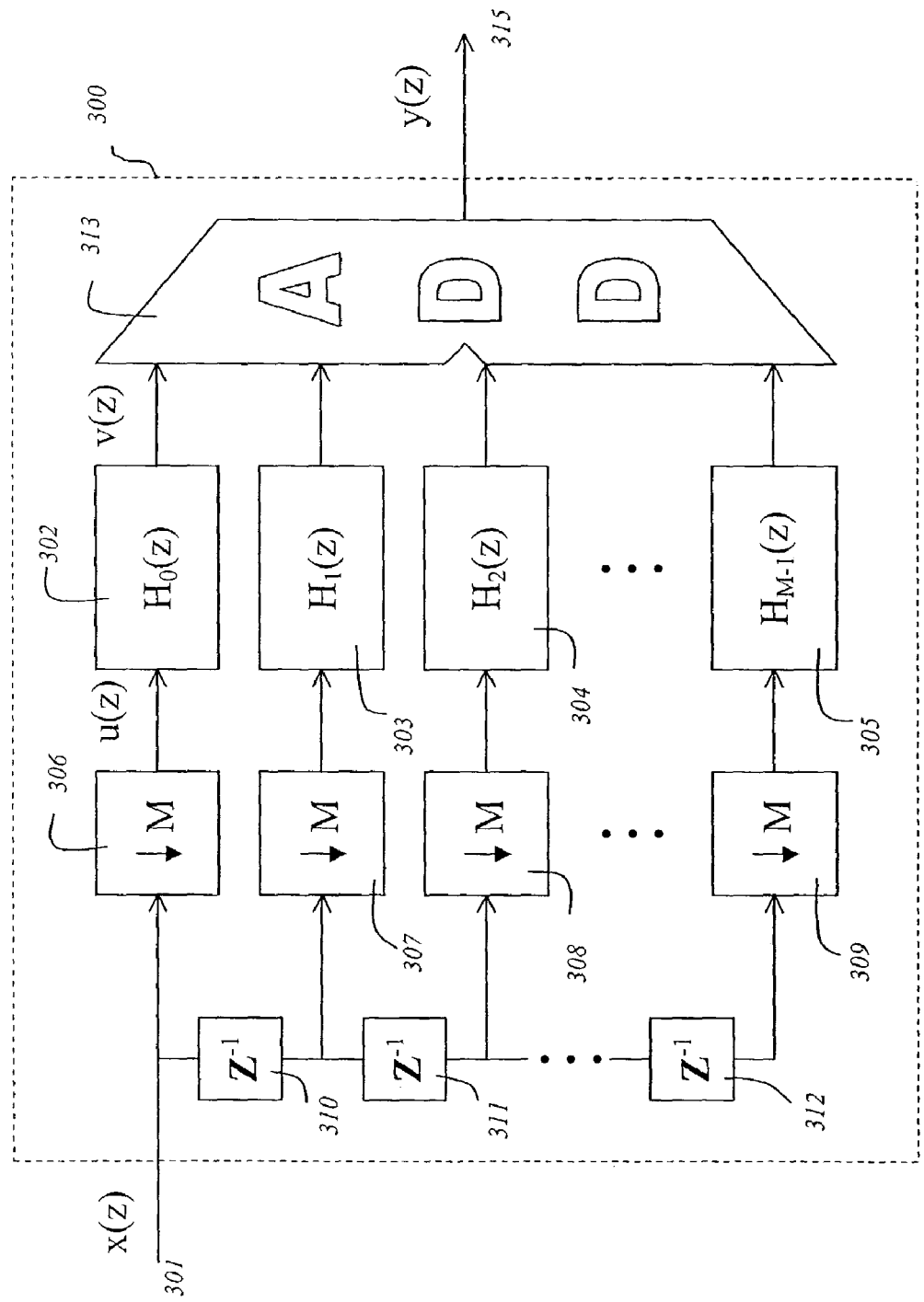
FIG. 3 is a block diagram of the filtering process used to perform the continuous wavelet transforms.

Non-stationary spectral analysis is used to process the corrected EKG signal. In a preferred embodiment, the continuous wavelet transform is applied to the corrected EKG signal (step 116). A software package operating on a digital signal processor can be used to perform this process, or alternatively, the processing in accordance with the present invention can be implemented using programmable logic and distributed arithmetic hardware. In a preferred embodiment of the present invention, the continuous wavelet transform is computed using a filter bank structure. The input to the filter bank is an evenly sampled, discrete-time waveform resulting from the EKG source after correction for ectopics. In a preferred embodiment, a sampling rate of 4 samples per second is used to adequately capture the subtle features of the waveform. FIG. 3 shows the filtering process performed in the filter bank structure 300 in accordance with the present invention. Before being fed into filter banks, the incoming signal 301 is divided using a combination of delay registers and down-samplers. A down sampler (306, 307, 308, 309) passes data through to its respective filter (302, 303, 304, 305) for samples arriving at integer multiples of a predetermined factor M of a sampling clock, but prevents the passing of all data in between such times. A series of delay registers (310, 311, 312) store the incoming data and present the output at the subsequent clock cycle. The result of combining the down samplers and delay registers is to distribute the input data to several filters, analogous to a card dealer who deals a deck of cards to M players such that the first player receives the $1^{st}$ card, the $(M+1)^{th}$ card, the $(2M+1)^{th}$ card, etc.

The separated signal is fed to a number of parallel discrete filter banks 300. Several filters (302, 303, 304, 305) reside within each filter bank. The output of the filters is combined (313) within each bank to create an output array 315. The outputs arrays of the filter banks are then combined to form a complete matrix output. This filtering operation is more efficient than using a single filtering process. In addition, the filtering processes can be implemented in real-time using well known overlap-add FFT methods. The result is a two dimensional function that shows the variation of the power distribution input signal versus time and frequency. A horizontal slicing of the matrix given by the output of a particular filter corresponds to a one-dimensional wavelet filtering performed at a fixed scale s in accordance with the equation for CWT(n,f) set forth above. A vertical slicing across the various outputs yields an instantaneous spectrum of the signal. For example, in the preferred embodiment, a wavelet filtering is computed for a scale s(i) for i=0 to i=40, which corresponds to using 41 separate filter banks from an initial analysis frequency of f=²⁵⁶⁄₃₀₀Hz to a frequency of f=⅟300Hz, whereby the frequency resolution varies in accordance with the equation $$I = \frac{1}{\delta} \log_2\left(\frac{f_0}{\Delta f}\right),$$

as set forth above.

The result of applying the filtering process is to perform a continuous linear convolution of the input signal with the filter kernel. Accordingly, the filtering operation is performed with the incoming discrete-time sequence, which is then broken into smaller segments, with the convolution performed using an FFT on each segment. The results are combined to form a final signal that is equivalent to the result that would be obtained from a linear convolution of the filter kernel directly with the original signal.

The resulting wavelet power spectrum is then computed using the equation for $P_{CWT}$ as set forth above, and normalized in accordance with the equation for normalization as set forth above.

The process described herein has been described with respect to the input signal from the EKG source. The same continuous wavelet transform process is also applied to the signal obtained from the impedance pneumography source. The respiratory cycle would replace the corrected heart rate cycle. Using the signals from the pneumography source, the continuous wavelet transform process is used to calculate the respiratory power spectrum. From the results, the instantaneous respiration frequency (IRF) can be obtained. The instantaneous respiration frequency is obtained by locating the peak frequency of the respiratory energy function.

Once the power spectrum for the heart rate and respiration spectrum has been determined, the information obtained is compared with predetermined time- and frequency-domain heart rate variability standards previously developed by the medical community. These standards do not reliably monitor both branches of the autonomic nervous system independently. The heart rate and respiration spectrum information is also used to compute the real-time heart rate variability indices that can be used to independently monitor both branches of the autonomic nervous system. Both are to aid physicians in a better understanding of that patient's autonomic nervous system activity. From the frequency-domain standards previously developed, energy in the power spectrum in the frequency range from 0.04 Hz to 0.15 Hz is defined as the low frequency (LF) component, while energy in the frequency range from 0.15 to 0.4 Hz is defined as the high frequency (HF) component. LF energy is generally believed to reflect activity in both the sympathetic and parasympathetic systems, while HF energy is generally thought to reflect activity in the parasympathetic system so long as the respiratory frequency remains above 0.15 Hz. This is not always the case. The ratio of LF/HF based on the previously developed standards is used to better approximate the activity in the sympathetic system, again so long as the respiratory frequency remains above 0.15 Hz. For example, when the sympathetic activity is increasing, it has been observed that the LF/HF ratio also increases. In the preferred embodiment of the present invention, the LF component, the HF component, and the LF/HF ratio are all displayed on the output monitor (118 on FIG. 1). In a preferred embodiment, the output monitor also displays the results of well known time domain analyses (step 120) performed on the EKG signal.

A preferred embodiment of the present invention also provides real-time heart rate variability indices that can be used to independently monitor both branches of the autonomic nervous system. The low frequency area (LFa) is computed as the energy in the heart rate power spectrum between 0.04 and 0.1 Hz. This measurement is indicative of the activity in the sympathetic system. The respiratory frequency area (RFa) is computed as the energy in the heart rate power spectrum under the respiration peak frequency (IRF), calculated using a window whose bandwidth is proportional to the frequency of respiration. In a preferred embodiment, the window bandwidth is equal to 0.7 IRF. This measurement is indicative of the activity in the parasympathetic system. The ratio of these two parameters (LFa/RFa) is then computed. This measurement is indicative of the Sympathovagal Balance.

It is known that the RFa is a better measure of parasympathetic activity than the HF. This is one of the differences that distinguishes the previously developed standard measures from the present invention. By monitoring these additional indices, physicians are able to obtain a better indication of cardiovascular control system malfunctions that occur during the resting state.

In a preferred embodiment, the output monitor displays the LFa, RFa, and LFa/RFa ratio computations: 1) in digital format representing their averages over the periods of time that correspond to different patient activities, 2) in two-dimensional analog form as trend data representing the respective instantaneous time varying waveforms over the entire period comprising the different patient activities, and 3) in three-dimensional analog form representing the composite time-frequency variation of the patient's autonomic response over the entire period comprising the different patient activities.

The use of the method in accordance with the present invention allows for non-stationary spectral analysis. Using non-stationary analysis (e.g., continuous wavelet transforms), the testing period can be significantly reduced. An example of the testing process used is as follows: (a) a five minute initial baseline challenge or measurement is taken with the patient in a resting state to determine the resting levels of the sympathetic and parasympathetic activity, (b) a 1 minute relaxational deep breathing challenge is measured to determine the reflex responses of the parasympathetic levels, (c) a 1 minute and 35 second measurement is taken during which the patient performs a series of five short Valsalva maneuvers to determine the reflex responses of the sympathetic system, and (d) a five minute upright or standing challenge is conducted to determine postural reflexes levels of both the sympathetic and parasympathetic systems. In addition, intervening baseline measurements can be taken between the various challenges to permit the patient's autonomic nervous system to recover from the previous challenge.

The entire measurement process as described in the example above can be completed in approximately 15 minutes. This is significantly less time than required to obtain similar data using prior art techniques.

Significant information regarding the patient's sympathovagal balance (balance between the sympathetic system and parasympathetic system) can be obtained from comparing the results from the measurement process with clinical data. The results can include underactive paryasympathetic activity, which is indicated by a diminished respiratory frequency area (RFa) with a value below the lower $15^{th}$ percentile of control/normal. Similarly, overactive paraysmathetic activity is indicated by a high RFa with a value above the upper $85^{th}$ percentile of control normal.

The results of the measurement process can also show the presence of underactive sympathetic activity, which indicated by a diminished low frequency area (LFa) with a value below the lower $15^{th}$ percentile of control/normal. Similaryly, overactive sympathetic activity can be indicated by a high LFa with a value above the upper $85^{th}$ percentile of control/normal.

Furthermore, information regarding the autonomic reflex can be monitored and quantified. This can be done by first giving the patient a specific, controlled stimulus to trigger a specific autonomic reflex reaction. By measuring and quantifying the extent of the response, one can determine the integrity or close-loop response of the autonomic nervous system in response to the stimulus. For example, an underactive parasympathetic reflex response can be indicated by a diminished RFa with a value below the lower $15^{th}$ percentile of control/normal. Similarly, overactive parasympathetic reflex can be indicated by a high RFa with a value above the upper $85$th percentile of control/normal. The presence of underactive sympathetic reflex can be indicated by a diminished LFa with a value below the $15^{th}$ percentile of control/normal. Similarly, overactive sympathetic reflex can be indicated by a high LFa with a value about the upper $85^{th}$ percentile of control/normal.

In another example, Paradoxic Parasympathetics (an expected sympathetic reflex which is replaced by an abnormal parasympathetic reflex) can be determined by comparing the initial measured baseline to the measurements obtained during standing or Valsalva maneuvers. An increase in the RFa above the upper $85^{th}$ percentile of control/normal suggests the existence of Paradoxic Parasympathetics.

Information concerning other known conditions can also be suggested from the data collected during the testing process. For example, possible Orthostatic Intolerance can be indicated by a drop in the LFa. Orthostatic Hypotension is indicated by a decrease in LFa coupled with a drop in blood pressure that exceeds 20 mmHg in systolic and/or 10 mmHg in diastolic upon standing. Postural Orthostatic Tachycardia Syndrome is indicated by an increase in heart rate of more than 30 beats per minute or a sustained level of over 120 beats per minute upon standing.

The method in accordance with the present invention can be applied in various environments. In a lab setting, testing can be performed in a short period of time to determine any indication of the Orthostatic condition set forth above, as well any indication of syncope. In an operating room setting, continuous monitoring of the patient will be performed. Physicians can use data from the monitor output to provide feedback on the depth of anesthesia, hypovolemia, sudden cardiac death, and recovery from anesthesia. In a Neonatal Intensive Care Unit, monitoring the sympathetic activity, parasympathetic activity, and the sympathovagal balance, provides physicians with information to aid in the diagnosis of the onset of bradycardia and the maturity of the ANS. In an intensive care unit setting, testing can be performed over short periods of time to determine the same trend information as current 24 hour monitors provide. Typically, these short periods of time are only five to ten minutes long, and are taken four or five times per day.

The application of the method in accordance with the present invention provides for improved spectral analysis of heart rate and respiratory rate signals. Such analysis was formerly limited to primarily stationary data. By studying time-varying data in accordance with the present invention, the behavior of the autonomic nervous system can be monitored more closely and in greater detail than previously possible. The data can be collected, processed, and updated over shorter periods of time, making the information less sensitive to patient movements that might occur during the monitoring period. This allows for improved resolution and better separation of the processed signals, enabling responses attributable to the parasympathetic system to be more accurately distinguished from those attributable to the sympathetic system.

The practical benefits of non-stationary spectral analysis (including with the Continuous Wavelet Transform) of heart rate and respiratory rate signals is that it provides better time- and frequency-resolution of biological signals. This, in comparison with earlier methods using signal processing techniques that require stationary or quasi-stationary signals, including the FFT, autoregression, or short-time FFT analyses. The improved resolution in the analysis of the respective biological signals enables a better separation in the monitoring of the two autonomic nervous system branches (i.e., sympathetic and parasympathetic).

Non-stationary signal analysis of biological signals avoids the time-frequency compromise and permits the implementation of very short signal analysis periods. For example, in a preferred embodiment the spectral analysis is updated every 4 seconds as compared to previous applications that were updated every no more than every 32 seconds. This eliminates much of the signal averaging that is inherent in the previous methods. Thus, better separation, and shorter analysis periods provides much more detail regarding the activities of the two ANS branches, revealing more clinically relevant information.

The end result is a significant improvement in specificity regarding the activities of the two branches of the autonomic nervous system: 1) separately in response to individual challenges and 2) together in response to whole system challenges during periods of activity, and quiescent or static periods of rest. Improved specificity enables better differential diagnoses of patient populations and improved medical care of patients in general.

It should be understood that the foregoing is illustrative and not limiting and that obvious modifications may be made by those skilled in the art without departing from the spirit of the invention. Accordingly, the specification is intended to cover such alternatives, modifications, and equivalence as may be included within the spirit and scope of the invention as defined in the following claims.

We claim:

1. A method for measuring activity of the autonomous nervous system of a patient comprising the steps of:
   1) obtaining instantaneous heart rate signals of said patient;
   2) computing a first power spectrum from said instantaneous heart rate signals using non-stationary signal analysis;
   3) determining a level of sympathetic activity and parasympathetic activity from said power spectrum;
   4) obtaining respiratory activity signals of said patient;
   5) computing a second power spectrum from said respiratory signals using non-stationary signal analysis; and,
   6) determining the instantaneous respiration frequency from the said second power spectrum.

2. A method as set forth in claim 1, further comprising the steps of:
   7) computing a low frequency area from said first power spectrum;
   8) computing a respiration frequency area from said second power spectrum;
   9)) using said low frequency area to determine a level of sympathetic activity;
   10) using said respiration frequency area to determine a level of parasympathetic activity; and
   11) using the ration of said low frequency area to said respiration frequency area to determining a level of sympathovagal balance.

3. A method as set forth in claim 2, wherein step 6.5 comprises:
   11.1) comparing said ratio with a set of existing standards.

4. A method as set forth in claim 2, wherein step 2 and step 5 comprise computing said first power spectrum and said second power spectrum using analysis windows of four seconds or less.

5. A method as set forth in claim 4, wherein said level of sympathetic activity, said level of parasympathetic activity, and said sympathovagal balance are determined in a clinical setting using a test period of approximately 15 minutes and 35 seconds.

6. A method as set forth in claim 4, wherein said level of sympathetic activity, said level of parasympathetic activity, and said sympathovagal balance are determined in an operating room environment wherein patient monitoring is continuous.

7. A method as set forth in claim 4, wherein said level of sympathetic activity, said level of parasympathetic activity, and said sympathovagal balance are determined in a Neonatal Intensive Care Unit.

8. A method as set forth in claim 4, wherein said heart rate signals and said respiratory activity signals further comprise the steps of:
- 1.1) conducting a baseline test approximately 5 minutes in length to determine sympathetic level, parasympathetic level, and Sympathovagal Balance in a resting state;
- 1.2) conducting a relaxational deep breathing challenge approximately 1 minute in length to determine the reflex response of said parasympathetic level;
- 1.3) conducting a series of Valsalva maneuvers of approximately 15 seconds or less, wherein said series is approximately 1 minute and 35 seconds in length to determine the reflex response of said sympathetic level;
- 1.4) conducting a standing challenge approximately 5 minutes in length to determine said sympathetic level and said parasympathetic level in a orthostatic reflex.

9. A method as set forth in claim 8, further comprising the step of:
- 7) comparing the measurements of step 1.1 with the measurements of step 1.2, wherein the existence of overactive parasympathetic reflex is indicated when the respiratory frequency area measurement of step 1.2 is above the upper $85^{th}$ percentile of control/normal.

10. A method as set forth in claim 8, further comprising the step of:
- 8) comparing the measurements of step 1.1 with the measurements of step 1.3, wherein the existence of overactive sympathetic reflex is indicated when the low frequency area measurement of step 1.3 is above the $85^{th}$ percentile of control/normal.

11. A method as set forth in claim 8, further comprising the step of:
- 9) comparing the measurements of step 1.1 with the measurements of step 1.3, wherein the existence of Paradoxic Parasympathetics is indicated when the respiration frequency area measurements of step 1.3 is above the $85^{th}$ percentile of control/normal.

12. A method as set forth in claim 8, further comprising the step of:
- 10) comparing the measurements of step 1.1 with the measurements of step 1.4, wherein the existence of Paradoxic Parasympathetics is indicated when the respiration frequency area measurements of step 1.4 is above the upper $85^{th}$ percentile of control/normal.

13. A method as set forth in claim 8, further comprising the step of:
- 11). comparing the measurements of step 1.1 with the measurements of step 1.4, wherein the existence of Ortostatic Intolerance is indicated when the change in low frequency area measurements over the respiration frequency area measurements taken in step 1.4 is below the lower $15^{th}$ percentile of control/normal.

14. A method as set forth in claim 1, wherein said non-stationary signal analysis used in step 2 is continuous wavelet transforms.

15. A method as set forth in claim 1, wherein said non-stationary signal analysis used in step 5 is continuous wavelet transforms.

16. A method as set forth in claim 1, wherein step 1 is performed using a EKG.

17. A method as set forth in claim 1, wherein step 2 further comprises the steps of:
- 2.1) identifying ectopics within said heart rate signals; and
- 2.2) removing said ectopics from said heart rate signals.

18. A method as set forth in claim 1, wherein step 2 is performed using multi-rate filter banks.

19. A method as set forth in claim 18, wherein step 2 comprises the steps of:
- 2.3) down-sampling of said first power spectrum; and
- 2.4) poly-phase filtering of said first power spectrum.

20. A method as set forth in claim 1, further comprising the step of:
- 12) monitoring blood pressure of said patient.

21. A system for measuring activity of the autonomous nervous system of a patient comprising:
- a first source providing instantaneous heart rate signals of said patient;
- a signal processor coupled to said first source, said processor used to compute a first power spectrum of said heart rate signal using continuous wavelet transform techniques;
- an output coupled to said signal processor, said output providing a visual display of said first power spectrum; and
- a second source providing instantaneous respiration signals, wherein said signals are processed by said processor to obtain a second power spectrum, said second spectrum displayed on said output.

22. A system as set forth in claim 21, wherein said processor is a software program.

23. A system as set forth in claim 21, wherein said processors comprises programmable logic operating on distributed arithmetic hardware.

24. A system as set forth in claim 21, wherein said output comprises a video display screen.

25. A system as set forth in claim 21, further comprising a third source providing blood pressure data of said patient, said blood pressure data displayed on said output.

26. A system as set forth in claim 21, wherein said output displays the low frequency area, respiration frequency area, and the ratio of said low frequency area to said respiration frequency area as a continuous plot versus time.

27. A system as set forth in claim 21, wherein said output displays the low frequency area, respiration frequency area, and the ratio of said low frequency area to said respiration frequency area in digital format representing averages over periods of time.

28. A system as set forth in claim 21, wherein said output displays the low frequency area, respiration frequency area, and the ratio of said low frequency area to said respiration frequency area in three-dimensional analog form.

* * * * *

UNITED STATES PATENT AND TRADEMARK OFFICE
CERTIFICATE OF CORRECTION

| | | |
|---|---|---|
| PATENT NO. | : 7,079,888 B2 | Page 1 of 1 |
| APPLICATION NO. | : 10/387070 | |
| DATED | : July 18, 2006 | |
| INVENTOR(S) | : Oung et al. | |

It is certified that error appears in the above-identified patent and that said Letters Patent is hereby corrected as shown below:

Claim 2, column 12, line 44, should read as follows:
--9) using said low frequency area to determine a level of--

Claim 2, column 12, lines 48-49, should read as follows:

--11) using the ratio of said low frequency area to said
respeiration frequency area to determine a level of--

Signed and Sealed this

Twenty-first Day of November, 2006

JON W. DUDAS
*Director of the United States Patent and Trademark Office*